(12) United States Patent
Palumbo

(10) Patent No.: US 9,827,264 B1
(45) Date of Patent: Nov. 28, 2017

(54) METHOD AND SYSTEM FOR THE TREATMENT OF MEDICAL CONDITIONS BY INTRAVENOUS THERAPY

(71) Applicant: Wyatt J. Palumbo, Naples, FL (US)

(72) Inventor: Wyatt J. Palumbo, Naples, FL (US)

(*) Notice: Subject to any disclaimer, the term of this patent is extended or adjusted under 35 U.S.C. 154(b) by 0 days.

(21) Appl. No.: 15/150,754

(22) Filed: May 10, 2016

Related U.S. Application Data

(63) Continuation of application No. 14/230,401, filed on Mar. 31, 2014, now abandoned.

(51) Int. Cl.
| | |
|---|---|
| *A01N 63/00* | (2006.01) |
| *C12Q 1/00* | (2006.01) |
| *A61K 31/714* | (2006.01) |
| *A61K 9/00* | (2006.01) |
| *A61K 45/06* | (2006.01) |
| *A61K 31/4415* | (2006.01) |
| *A61K 31/16* | (2006.01) |
| *A61K 33/32* | (2006.01) |
| *A61K 33/30* | (2006.01) |
| *A61K 33/24* | (2006.01) |
| *A61K 33/04* | (2006.01) |
| *A61K 33/06* | (2006.01) |
| *A61K 31/145* | (2006.01) |
| *A61K 31/405* | (2006.01) |
| *A61K 38/06* | (2006.01) |
| *A61K 31/198* | (2006.01) |
| *G06F 19/00* | (2011.01) |

(52) U.S. Cl.
CPC .......... *A61K 31/714* (2013.01); *A61K 9/0019* (2013.01); *A61K 31/145* (2013.01); *A61K 31/16* (2013.01); *A61K 31/198* (2013.01); *A61K 31/405* (2013.01); *A61K 31/4415* (2013.01); *A61K 33/04* (2013.01); *A61K 33/06* (2013.01); *A61K 33/24* (2013.01); *A61K 33/30* (2013.01); *A61K 33/32* (2013.01); *A61K 38/063* (2013.01); *A61K 45/06* (2013.01); *G06F 19/3431* (2013.01)

(58) Field of Classification Search
CPC .................................. A01N 63/00; C12Q 1/00
See application file for complete search history.

(56) References Cited

U.S. PATENT DOCUMENTS

2013/0064803 A1* 3/2013 Naidu .................... A61K 45/06
424/94.6

OTHER PUBLICATIONS

Berndston et al. (Mold Toxicity or Chronic Inflammatory Response Syndrome (CIRS). Practice Report, pp. 1-7, 2012).*

* cited by examiner

*Primary Examiner* — Scott Long
*Assistant Examiner* — Natalie Moss
(74) *Attorney, Agent, or Firm* — Livingston Loeffler, P.A.; Edward M. Livingston, Esq.; Bryan L. Loeffler, Esq.

(57) ABSTRACT

A method and system for identifying and treating various medical conditions caused by toxins, pathogens, hormonal imbalances and other factors involving intravenous therapy.

16 Claims, 2 Drawing Sheets

METHOD AND SYSTEM FOR THE TREATMENT OF MEDICAL CONDITIONS BY INTRAVENOUS THERAPY

FIELD OF THE INVENTION

This invention relates to the field of medicine and more particularly, a method and system for treating medical conditions caused by toxins, pathogens, hormonal imbalances and other factors using intravenous therapy. This invention focuses on the underlying causes of medical conditions rather than conventional methods, which only focus on treating the symptoms that manifest after exposure to the underlying causes of the medical conditions.

BACKGROUND OF THE INVENTION

Medicine today has created a myriad of diagnoses that are truly symptoms of more deeply rooted underlying causes. Medicine uses various diagnoses in attempts to provide solutions for individual ailments; however, if a true diagnosis is not reached, conventional methods of treatment will just mask symptoms and not fully alleviate the condition, nor provide a long term solution.

For example, does a diagnosis such of fibromyalgia actually address an underlying cause? Overactive nerves are the typical definition given to patients for this ailment. However, the problem with that response is that "overactive nerves" are not an underlying cause. Rather, "overactive nerves" are just a symptom of the underlying cause. The correct question that should be asked is "Why are your nerves overactive?" Questions such as these must persist by patients and physicians until an actual cause is discovered. Unless the actual cause of an ailment is determined and treated, a patient will never truly be cured of the ailment.

Therefore, a need exists for a transformative method and system that provides individuals with not only a simplified outlook into medical diagnostics, but a step by step procedure for identifying and treating various medical conditions commonly seen throughout medicine today so that the actual ailment is treated and not just the symptoms that arise as a result of the ailment.

SUMMARY OF THE INVENTION

The primary object of the present invention is to provide a method and system that provides individuals with not only a simplified outlook into medical diagnostics, but a step by step procedure for identifying and treating various medical conditions commonly seen throughout medicine today so that the actual ailment is treated and not just the symptoms that arise as a result of the ailment.

An additional object of the present invention is to provide a method and system that is a minimalistic, as necessary approach that ends once a patient has revealed his or her primary symptoms/complaints are lifted and the patient feels he or she can return to his or her environment and regain his or her physical health.

The present invention fulfills the above and other objects by providing a method and system wherein the first primary idea is to provide a quantitative objective approach to diagnoses of many different biochemicals including, but not limited to, neurotransmitters, amino acids, hormones, and mycotoxins. Specific values and patterns of these data are easily correlated and discernable. These quantitative data lead to indications that will directly coincide with patient cues. These objective data serves as tools to guide treatment as well as show improvement following administration of the 3 Phases of treatment. Once an individual says that he or she regained their physical health and can return to their environment, treatment may cease.

A second aspect of the invention encompasses the time at which each diagnosed causality (through the quantitative data collected in the first primary idea) is addressed. This step is key to the success rate of said treatment; each causality must be addressed in a specific order. If causalities are addressed at improper times, treatment will fail, and in some cases may be dangerous to the patient.

A third aspect of the invention is the treatment of the individual which may have up to three treatment phases.

The method and system of the present invention may be used independently as the primary form of treatment to treat many ailments such as anxiety, bipolar II disorder, chronic fatigue syndrome, chronic migraines, depression, fibromyalgia, idiopathic seizures (IS), insomnia, irritable bowel syndrome, pathogenic infections, toxicity, and so forth (and any co-morbidity of said ailments). In addition the method and system of the present invention may be used in conjunction with therapies for entities such as stem cell therapy, neurodegenerative disease, and brain trauma. Whether it is used as the primary form of treatment or in conjunction with a preexisting therapy, the quality of life can be improved in nearly all individuals regardless of the ailment.

Doctors providing treatment focus on one bodily system or one specific symptom when treating nearly all conditions; however, the human body does not function as an individual system. Rather, it functions together as a whole with multiple systems each playing a role in modulating the brain and body.

In terms of treating underlying causes versus the symptoms, one can think of a tree with many branches and large roots; if one branch is cut, the tree can survive. Even if many branches are severed, the tree will stagnate shortly, but survive and grow nonetheless. Symptoms are like branches; if one or more is alleviated, it is merely a short term solution as eventually the underlying cause will persist, thereby presenting more symptoms and more branches growing even stronger than before. To treat an ailment successfully, one must sever the roots of the underlying cause to provide a successful long term solution.

Treatment is unique to each individual; though, the process remains the same. One must understand that the brain and body must be restored to equilibrium, a "baseline", in order to allow the body to function as it was originally intended. The term "baseline" will be used herein as a term that refers to applying the same concept and treatment to each patient (through Phase 1), thus bringing each individual to the "same" level. Once this level is reached, any symptom that persists through the baseline proves to be a true symptom—a symptom that was not masked by toxicity, malnutrition, and irregularities in the brain's electrical circuitry. Causality diagnostics are then applied to discover the root cause of said symptom.

BRIEF DESCRIPTION OF THE DRAWINGS

In the following detailed description, reference will be made to the attached drawings in which.

DESCRIPTION OF THE PREFERRED EMBODIMENTS

Figure 1:
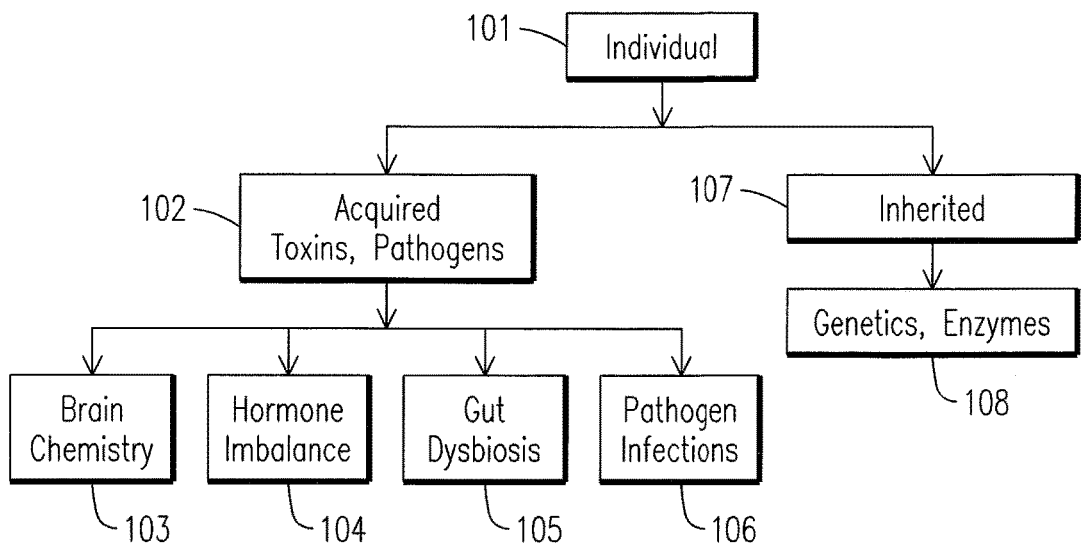
FIG. 1 is a block diagram illustrating patient abnormalities which are treated using the method and system of the present invention.

The term "toxicity" or "toxins" will be used herein as a term that refers to excess fat-soluble toxins that are present in the brain and throughout the body. Water soluble toxins are not a primary concern as they readily dissolve in water and are excreted through the urine. Fat soluble toxins are encountered frequently and are of primary concern in the method and system of the present invention. These toxins are mainly volatile organic compounds (VOCs) such as mycotoxins (toxins produced by mold species), benzene, toluene, and mandelic acid, among others. Other VOCs can either not be tested for, or are not of great abundance in the body. However, the mechanisms at which these toxins are removed remain the same; therefore, nearly all toxins, no matter the abundance, will be removed through Phase 1 of treatment.

The treatment of Phase 1 focuses on a combination of intravenous (IV) therapy of naturally occurring ingredients with hand selected natural supplements based on an abundance of correlated objective quantitative data that coincides with feedback from the patients themselves. This constitutes the majority of Phase 1 of this treatment. The other constituents of Phase 1 include all the quantitative testing as well as mold spore analysis of one's home to ensure proper causalities are being identified and subsequently addressed.

IV therapy is the choice of action due to its high efficacy and absorption rate as it enters directly into the bloodstream, as opposed to oral supplementation that has to bypass the stomach and enter the intestines where it is absorbed and distributed to the rest of the body. A few oral supplements are still utilized, either due to no IV availability, or to help promote sleep and restoration in the evening.

Phase 1 of treatment and the IV therapy's primary emphasis relies on restoring the brain's electrical activity, as the brain, although working together with other bodily systems, controls the majority of electricity throughout the brain and body, which directly causes the majority of problems in any individual.

When toxicity is prevalent in an individual, the brain, an electrical organ, responds by increasing the production of excitatory neurotransmitters, such as glutamate, dopamine, norepinephrine, epinephrine, and histamine. As these excitatory neurotransmitters rise, the brain responds by increasing its inhibitory (calming) neurotransmitters to counteract this effect. Primary inhibitory neurotransmitters that are of concern include gamma-aminobutryic acid (GABA), serotonin, and taurine.

As toxin storage begins to increase due to genetics (as discussed later), the inhibitory chemicals become depleted over time causing excess electricity to be sent throughout the brain and body. Excess glutamate (excitatory neurotransmitter) causes calcium influx into the cell and thus eliciting action potentials which are electrical signals that allow for cell communication and movement as well as other functions.

Too much influx will cause unwanted and dangerous abnormalities due to excess electricity such as anxiety and insomnia, symptoms of an overactive brain. "Overactive brain" will refer to excess electricity in specific brain regions while "underactive brain" will refer to diminished electrical activity in specific brain regions. Both an overactive and underactive brain can occur simultaneously.

For an overactive brain, symptoms of ailments such as chronic pain and fibromyalgia will be further exasperated by excess calcium influx because as the brain becomes over electrified it becomes more sensitive to incoming pain signals.

The primary objective is to lower these excitatory chemicals and increase the inhibitory chemicals, thus preventing this unwanted, electricity. The term "Calming the Brain" will be used to refer to this latter objective herein. This task is accomplished by direct IV infusion with amino acids, minerals, vitamins and so forth that contribute to restoring the brain's electrical activity. The IV infusion therapy for Phase 1 of treatment will be referred to herein as "Phase 1 IV drip."

The two supporting mechanisms at which calming the brain is accomplished is by the IV therapy's 2 secondary objectives—replenishing nutrition and toxin removal. "Replenishing Nutrition" will refer to replenishing much needed vitamins, minerals, amino acids, co-factors, and antioxidants.

"Toxin Removal" will refer to ridding the body of toxins through direct and indirect mechanisms. Direct mechanisms include ridding of these toxins with infused IV glutathione that donates its sulfhydryl group to help break bonds of toxins to allow for secondary metabolites that can be excreted in the urine. For example, trichothecene, the most potent of the mycotoxins, has an epoxy group within its structure that helps contribute to the stability of the compound, thus making it extremely difficult to rid of this mycotoxin as it rapidly depletes glutathione levels upon entry. In a chemical reaction, glutathione donates its sulfhydryl group to break the epoxy ring on trichothecene which results in a secondary compound that is easier to excrete in the urine.

Indirect mechanisms include removing unwanted consequences that result from excess toxicity. This takes place by replenishing nutrition in addition to the IV glutathione. These toxins generate free radical oxygen species (ROS) that cause oxidative stress on the brain. In addition these mycotoxins have been known to cause damage to the brain's astrocytes, endothelial cells, and neural cells. If left untreated, this oxidative stress can result in damage to the brain and the myelin sheath, the insulating material that coats the neurons and allows for electrical insulation for cell to cell communication. Additionally, if the astrocytes are damaged, the blood brain barrier can become altered resulting in even more devastating consequences. Another primary use for glutathione is to remove these ROS and thus prevent oxidative stress and other damaging consequences in the brain.

Both of these direct and indirect mechanisms help contribute to the primary objective of calming the brain. Replenishing nutrition not only allows for the building of proteins, but many vitamins and minerals are involved as co-factors in numerous chemical reactions in the brain and body. Co-factors are entities that promote the forward phase of any given reaction; therefore, they are vital in restoring the brain's electricity. Both replenishing nutrition and toxin removal will help address the primary concern of calming the brain which will substantially contribute to the long term success of the patient.

The primary emphasis of Phase 1 of treatment is accomplished in summary by the aforementioned sections. If symptoms persist through Phase 1, and do not allow for the patient to regain their health, Phase 2 of treatment will ensue. Phase 2 includes full optimization including bioidentical hormone replacement therapy. Bioidentical hormones are used as they are of the same biochemical structure as naturally occurring hormones made in the body. Many individuals do not need Phase 2 as toxin-induced hormonal suppression is frequently alleviated by Phase 1; therefore, it is only used as necessary.

Phase 3 of treatment consists of eradication of bacteria, infections, and pathogens. "Pathogens" will refer to bugs, mainly tick-borne infections such as Lyme, *babesia*, and *bartonella*, among others. Phase 3 consists of two sub-steps. As aforementioned, these sub-steps must be addressed in order to ensure success and safety in the patient. The first sub-step in Phase 3 is to heal and cleanse the gut of toxic materials and replenish the beneficial bacteria while cleansing the intestines and colon and reassuring the gut lining. "Toxic materials" refers to bad bacteria such as *Klesbiella* and *Proteus* among others, as well as *candida* toxins. "Beneficial bacteria" refers to the good bacteria such as *lactobacillus* and *bifidobacterium* among others.

Sub-step 1 of Phase 3 is accomplished through natural ingredients of various hand-selected supplements that destroy the toxic materials, replenish the beneficial bacteria, heal the gut lining, and cleanse the body and gastrointestinal tract over an approximate 10-20 week (or more) process. The "gut" which encompasses not only the intestinal tract, but the stomach and its lining, and the colon, is by no means fully healed after the 10-20 week process; however, substantial improvements can be seen in this time period. These improvements will allow the gut to continue to heal on its own over approximately the next 1-3 years (or more).

Pathogenic eradication is the next and final step to Phase 3. Commonly encountered pathogens include Lyme, *babesia*, and *bartonella*, among others. As with toxins, not every pathogen can be identified; however, the process of their eradication is the same. IV therapy of mega dose vitamin C (15,000-100,000 mg) will be used interspersed with the Phase 1 IV drips over approximately a 6-16 week period. As with the gut, this does not fully eradicate the pathogens, but one's immune system can alleviate the remaining pathogens over time as these pathogens are no longer guarded by their protective biofilms.

Most individuals spend 20, 30, even 40 years or more growing unhealthier, either by merely living in this country, being exposed to toxins and pathogens, or through failed treatment attempts to restore their health. The method and system of the present invention can not only diagnose and treat the true causes of his or her ailments, but it can also be used as a primary form of treatment to correct and heal the damages caused by failed treatments from other doctors.

The method and system of the present invention regarding diagnostics can be simplified into two fundamental concepts—inherited and acquired abnormalities. "Inherited" will refer to entities such as genetics and enzymes while "acquired" will refer to toxins and pathogens and their resulting consequences.

Toxins, specifically mycotoxins (produced from mold species), cause suppression of the immune system which allows for pathogens to enter the body; therefore, mold toxicity is a term that will be used to describe excess toxicity caused by mycotoxins. This is the commonality among nearly all health ailments. The treatment for mold is addressed first, and is accomplished by the Phase 1 IV drip used to calm the brain, replenish nutrition, and remove toxins as well as the mold spore testing in the patient's environments.

These toxins and pathogens 102 cause imbalances throughout the brain and body of an individual 101; these acquired consequences can be simplified into four categories, as illustrated in FIG. 1:

1) Brain Chemistry 103
2) Hormonal Imbalance 104
3) Gut Dysbiosis 105—Nutritional Deficiencies
4) Pathogenic Infection 106

These four terms will be discussed later when they reappear throughout this invention. However, a brief understanding of medical diagnostics, the two fundamental concepts—inherited and acquired, will be discussed next. Treatment will be depicted last after all background information is discussed to help illustrate the viewpoint and conclusions of this invention.

There is a specific schedule and order of treatment that each defined causality must follow. Each person is different and treatment protocols should take that into account; however, this uniqueness primarily affects the quantity of elements involved in said treatment, but not the schedule of treatment. As with each system in the body, each underlying cause is intertwined with one another.

Any abnormality can be traced back to two fundamental concepts—either Acquired or Inherited 107. "Inherited" refers to traits such as genetics and enzymes 108, as illustrated in FIG. 1. Genetics are referring to researched, pinpointed, and specific genes that play a role in homeostasis in the brain and body. Enzymes refer to the biochemical intermediates in a chemical reaction that help catalyze the reaction to proceed in a forward fashion. Both affect the brain's electricity.

"Acquired" includes effects from the environment that has been aforementioned as toxins and pathogens which branch into four categories.

Genes (inherited) serve as a tool to help guide treatment protocol; however, at this time, genes can't be manipulated in a fashion that reverses their effect (or to alleviate the effect in any manner). Thus, they help increase awareness of the patient's condition, but cannot serve as a primary means of treatment.

On the other hand, the acquired abnormalities provide the means for treatment. As previously discussed, the underlying concept behind acquired ailments is only two possible sources—toxins and pathogens.

These two fundamental concepts will serve as the basis for this invention and the method and system of the present invention which will show that all ailments trace back to these two notions.

There are various genes that have been identified as risk factors for many conditions, such as the serotonin transporter gene, which is a link for depression and decreased serotonin. Some of these genes can be pinpointed, but serve little purpose in treating individuals. However, the most impactful gene, a subset of HLA-DRB-DBQ genetics, is not widely known and is directly associated with environmental toxin toxicity—specifically mold toxicity.

The medical field recently pinpointed the dramatic consequences to a subset of HLA-DRB-DBQ genetics. People with this subset cannot build antibodies to any of these toxins, including mycotoxins. In other words, their bodies cannot locate and eliminate these toxins from their systems. This allows for massive storage of toxins which poses alarming issues throughout the brain and body.

This storage causes an increase in excitatory neurotransmitters with subsequent increase of inhibitory neurotransmitters. The increase of excitatory chemicals, specifically glutamate, causes calcium to enter the cell and elicit action potentials thus increasing the electricity in the brain and body. As the toxins continually enter the system with no direct mechanism of excretion, they will plummet the inhibitory neurotransmitters and cause further increases in electrical activity as well as damage to the brain.

Mold toxicity has an inherited diagnosis through the subset of HLA-DRB-DBQ genetics; however, since it is acquired through the environment it will be referred to as one of the two concepts that cause the four main ailments associated with acquired abnormalities.

Since inherited traits merely serve as tools to help understand more about one's genetics, the acquired abnormalities serve as the primary basis for diagnostics and treatment. Luckily, toxins and pathogens have led to the generation of diagnostic testing that can be utilized to diagnose specific causalities.

Toxins, specifically mycotoxins, are tremendously abundant with an estimated 30-50% of homes and buildings saturated with these toxins. Many are familiar with mold; however, most are unfamiliar with its immense impact upon one's health. Additionally, everyone knows not to eat foods with mold growth on them, but many are unaware that breathing/inhaling the mycotoxins that these species produce is significantly more harmful than ingesting them.

Proper mold remediation requires protective goggles, ventilation suits, and filtered breathing devices to protect against harmful mycotoxins such as the black mold toxin. For remediation of mold, the Occupational Safety and Health Administration (OSHA) additionally recommends that your body be covered from head to toe including boots, long clothing, and head covering in conjunction with the protective goggles, suit, and breathing devices to prevent any contact with these mold toxins.

Many believe that in order to have a substantial effect on one's health, the exposure to mold must be as evident. However, mold is like an iceberg; if you can see it, that's only 10% of what's there and approximately 90% of the mold exposure is hidden in the walls, secreting its harmful toxins throughout your home and into your body.

Mold does not discriminate; it is found in dry states like California and Arizona, and humid states such as Florida. Although the likelihood of mold exposure dramatically increases with older homes, mold can be found everywhere including new homes as it longs for any conditions that promote entities such as high moisture and cellulose consumption (dry wall, ceiling tiles, etc.).

Susceptibility through the aforementioned subset of HLA-DRB-DBQ genetics makes toxins like mycotoxins quite dangerous. A primary detrimental effect of any toxin especially mycotoxins, is their ability to suppress the immune system, thus causing substantial imbalances in brain chemistry, hormones, and intestinal flora, in addition to allowing harmful pathogen entry to the body.

The second concept of acquired abnormalities is pathogens, such as Lyme disease, *babesia*, and *bartonella*, require the immune system to be compromised allowing entry to the body. Thus, toxicity remains the commonality among the majority of all patients. These infections are not only tick-borne, but numerous studies including information from the Michigan Department of Natural Resources have proved that, "Other species of ticks such as the dog tick or wood tick, the lone-star tick and the rabbit tick, and biting insects such as mosquitoes, deer flies and horse flies have been shown to carry the Lyme disease bacterium".

There has been an alarming increase of tick-borne infections such as Lyme disease; however, many studies show that only a compromised immune system allows for entry of these pathogens. Therefore, many who are infected and carry these diseases have been exposed to toxins at some point prior to infection.

Once these pathogens have entered the body, their eradication is quite difficult; however, the toxins, brain chemistry, hormones, and gut toxicity must be addressed and treated prior to these pathogens to rebuild the immune system, replenish nutrition, and calm the brain to restore homeostasis in the brain and body which are taking direct onslaught from the aforementioned various toxins as well as these biofilm producing pathogens.

As aforementioned, the underlying concept is, that these toxins and pathogens can cause an array of problems; however, these problems can be grouped into four major topics, as illustrated in FIG. 1.
1) Brain Chemistry
2) Hormone Imbalance
3) Gut Dysbiosis (Imbalance)—Nutrition
4) Pathogenic Infection—Lyme Disease, *Bartonella*, etc.

More information on mold toxicity will be discussed first as it serves as the primary causality for the four acquired abnormalities.

Many people are aware of detrimental substances such as asbestos, formaldehyde, and tobacco smoke; however, mycotoxins, although well-researched (as will be outlined in this article), are widely unknown to the general population.

The three most well-known and abundant mycotoxins that are primarily discussed (due to testing access to these three mycotoxins) are Aflatoxin, Ochratoxin, and Trichothecene. The concept of Sick Building Syndrome was first recognized in 1982, but today it is better known as mold toxicity.

Nearly all individuals display an effect to mycotoxins; however, if one does not present the subset of HLA-DRB-DBQ genetics, these toxins are excreted when the individuals leaves this environment. For the individuals with this genetic subset, storage occurs frequently and thus causes a higher occurrence of the ailments associated with mold toxicity that are outlined below.

The reason this invention holds validity in the great abundance of individuals affected by mold toxicity is because of its vast profusion seen throughout this nation. In the early 1970s, energy conservation was a major issue in more industrialized nations. This energy crisis caused many changes in the construction of homes and building throughout the world, especially the United States.

Buildings and homes were designed with recycle ventilation to reduce energy costs as well as large buildings that were constructed windows that are permanently shut to better control temperature. Additionally, more inexpensive and lighter weight materials were developed and utilized in order to lower the amount of energy needed—cellulose based ceiling tiles and drywall, which mostly consist of recycled paper products that were used to save money.

Water damage/leaks affect nearly everyone at one point or another, and the problem with utilizing these cheap lightweight materials is that they are susceptible to mold growth. Many common mold species such as Stachybotrys consume organic materials like cellulose and drywall as a food supply.

Recent studies indicate that individuals spend nearly 90% of their time indoors, making them even more susceptible to these toxins. Many reasons contribute to why individuals suffer from this syndrome; however, there are a wide variety of serious health ailments associated with these toxins that affect nearly every bodily system.

Genetic research has pinpointed a subset of a gene (HLA-DRB-DBQ) that plays a major role in this ailment. There are a few types of this subset; however, if one does in fact have this gene, their bodies cannot produce antibodies to these toxins, and subsequently, these individuals move these toxins out of their body 465 times slower than people without the genes. In other words, these individuals with this gene store fatty toxins at a substantially more significant rate than people without the gene.

Although the most abundant fatty toxin that individuals will come into contact with are mycotoxins, these individuals cannot build antibodies to any fatty toxins including benzene (commonly found in tobacco smoke), toluene (commonly found in paint products), mandelic acid (biproduct found in Acutane acne medication), and any other VOC.

Mycotoxins have been documented to greatly affect mitochondria and thus energy production. Additionally, they have been known to inhibit DNA and RNA synthesis as well as cause damage and mutations to the DNA.

Many studies have been performed regarding mycotoxins and the immune system; however, their most impactful effect remains immunosuppression. These toxins have also, been known to cause asthma, allergic reactions as well as hypersensitivity. Mechanistically, mycotoxins have caused changes in TNF-alpha, one of the main regulators of the immune system, as well as changes in IgE.

In addition to the aforementioned effects, mycotoxins increase the toxic bacteria in the gut as well as cause inflammation in the gastrointestinal tract (GI). Additionally, it has been proven to cause diarrhea, vomiting, nausea, and abdominal cramps.

In terms of the endocrine system, mycotoxins have been proven to affect two primary hormones, progesterone and testosterone.

The brain is tremendously affected by mycotoxins. Its main effects include damage of the astrocytes (thus the blood brain barrier (BBB)), brain endothelial cells, and the neural cells causing cell apoptosis and oxidative stress to the brain. Three different studies also showed that mycotoxins can cause pituitary adenomas.

Other regions affected by mycotoxins include the joints (chondrocytes), pancreas (pancreatic lesions), liver (cancer), kidneys (damage), and the heart (cardiomyocytes) as well as causing myocardial lesions.

In terms of medical conditions, mycotoxins have been directly linked to Attention Deficit Disorder (ADD), Depression, and cognitive impairment equivalent to that of a minor traumatic brain injury.

As aforementioned, mold toxicity allows for pathogen entry. Both toxins and pathogens cause four distinct abnormalities seen in the brain and body. The first is "Brain Chemistry," which is a term that will be used to describe the state of neurotransmitters in the brain and their relationship to specific brain regions and subsequent bodily systems. The human brain is both a chemical and an electrical organ consisting of more than 100 billion individual nerves called neurons.

Since the brain contains neurons with mini-storage units called vesicles that store neurotransmitters, these neurotransmitter are the primary focus of this topic. Neurotransmitters travel between brain neurons serving as chemical messengers and activate specific receptors on brain neurons. Excitatory chemicals increase electrical activity in brain neurons while inhibitory neurotransmitters decrease electrical activity in brain. A simple neurotransmitter analysis coupled with an amino acid assay can reveal a multitude of indications in the brain which can be grouped into two categories—overactive and underactive.

Although there are many regions of the brain which play a role in health ailments, there are two primary regions, the anterior cingulate gyms and deep limbic system, which play a tremendous role in diagnostics and possible treatments.

Anterior Cingulate Gyrus System (ACS) and Deep Limbic System (DLS)

The ACS is located near the corpus callosum (divider between the left and right hemispheres of the brain) is responsible for a wide variety of functions. The ACS's involvement in mood changes, depression and anxiety disorders, pain perception, and many other cognitive and emotional functions is now well established; however, many diagnostics do not focus on this brain region.

The deep limbic system (DLS) is a walnut sized region located in the midbrain that serves as our emotional center. The deep limbic is called the emotional center because it stores our emotionally charged memories from childhood on. The deep limbic system is actually slightly largely in females than males, making the associated ailments more exemplified in females.

Both of these brain regions cause patients to worry excessively, have feelings of hopelessness in conjunction with lack of motivation, display symptoms of a racing brain, are opposed to change, have excess pain, and carry excessive guilt. Many of these subjective cues directly coincide with the below overactive associated "diagnoses".

Single Photon Emission Computed Tomography (SPECT) scans, although not widely accepted in the medical community, do reveal overactive and underactive regions in the brain. However, enough scans have been performed to link quantitative neurotransmitter and amino acid values; thus patients do not need to expose themselves to the radiation of the scan nor the high cost.

Overactive Associated "Diagnoses"
Addiction
Anxiety
Bipolar Disorder
Chronic Pain
Fibromyalgia
Insomnia
OCD
Seizures The medical community accepts these above ailments as diagnoses; however, there are true causes for these conditions, one of which is overactive brain chemistry. Diagnoses serve merely as another tool to help find true underlying causalities. Now, even overactive brain chemistry must be further questioned because it stems from an actual underlying cause such as toxicity, pathogens, and genetics.

Brain scans can indicate excess electricity throughout the brain; however, it does not identify a primary problem; it merely indicates that there is a problem. Specific brain regions can be pinpointed; however, scans can only serve as a guide, but not a direct diagnostic tool.

As with the overactive brain, there are two primary regions associated with the underactive brain. These two regions are the nucleus accumbens (pleasure center) and the prefrontal cortex (PFC—executive functioning, personality).

Nucleus Accumbens (NA)

The nucleus accumbens serves as our brain's reward center. In addition this brain region functions as our pleasure center, hunger center, and sex drive center. When underactive, one finds it difficult to get excited or even smile, usually suffering from symptoms of depression. In addition, since food releases dopamine, many will seek refuge in eating to boost their reward center to feel more "normal".

Activities become dull and uneventful. Many will stop exercising and taking care of themselves; depression can lock individuals into a seemingly endless loop of "going through the motions," never feeling a sense of accomplishment regardless of the magnitude.

Some will look to other entities such as drugs or alcohol to help boost and "self-medicate" their problems as these substitutes readily boost dopamine in the nucleus accumbens. Sometimes, even receiving gifts and presents does bring joy to oneself. Many find it difficult to smile. Associated neurotransmitters involve primarily dopamine, however many neurotransmitters including GABA and serotonin provide strong roles as well.

This brain region is the executive center of the brain, and has also been shown to relate to cognitive and social behavior as well as the planning of thoughts and goals. "The prefrontal cortex guides behaviors, thoughts, and . . . working memory" The PFC serves as the executive center for the brain. In other words it aids in, "the ability to inhibit inappropriate behaviors and thoughts, regulate our attention, monitor our actions, and plan and organize for the future". Although numerous neurotransmitters are involved, the primary neurotransmitter is dopamine.

Underactive Associated Diagnoses
ADD/ADHD
Addiction
Brain Trauma
Chronic Fatigue
Depression
Obesity As with the overactive diagnoses, these above ailments are actually indicators of true underlying causes (see final paragraph of the overactive section).

Many who suffer from these conditions think that it is their fault, and that their choices are the root cause of these ailments. Since the PFC controls the 4-second-memory, many individuals suffering from an underactive PFC find it difficult to remember new information. The mind plays a significant role in determining choices; however, without the proper tools (neurotransmitters, hormones, amino acids, etc), these decisions become exceedingly difficult.

Many find it difficult to get out of bed and some remain there for hours. Some overeat or "self-medicate" with drugs or alcohol to help compensate for the lack of dopamine to help stimulate these underactive brain regions. Nicotine releases an abundant amount of dopamine, and it is common to see an underactive brain region stimulated through smoking cigarettes.

Brain Trauma is a growing topic of interest in the field of medicine. Since the brain remains the most unknown organ of the body, it is extremely difficult to correct these abnormalities seen in Brain Trauma. However, an abundance of other health ailments are also associated with this issue as well that remained substantially overlooked.

This invention can improve brain function and thus help with brain trauma; however, all Phases of treatment are usually necessary in conjunction with other already existing therapies. Although, many of these ailments can be diagnosed easily and addressed before the trauma is ever treated and help the body return to a baseline where more treatment can ensue.

Numerous neurotransmitters have been correlated to not only brain scans, but subjective patient cues as wells. The neurotransmitters that play a major role in an overactive and underactive brain have been identified as both excitatory and inhibitory neurotransmitters.

Through thousands of correlated neurotransmitter profiles, the excitatory chemicals that exhibit the majority of the role in overactive and underactive brain regions are primarily glutamate, histamine, dopamine, norepinephrine (noradrenaline), epinephrine (adrenaline), GABA, serotonin, and taurine.

Glutamate is the brain's number one chemical (in quantity), encompassing almost half of all neurons, and is the primary excitatory chemical in the brain. Excess glutamate causes excess calcium influx into the cell, and in turn causes more voltage to be sent throughout the brain and subsequently the body.

It is the most dangerous excitatory chemical and has been linked with every health ailment on the planet including neurodegenerative diseases such as Alzheimer's, Parkinson's, ALS, and Huntington's as well as neurological conditions such as depression and anxiety.

If glutamate is in excess for a prolonged amount of time, it will cause cell death and can contribute to brain damage through oxidative stress pathways in addition to the aforementioned health ailments. Glutamate gives rise to such vast amounts of electricity that its suppression is a primary priority in the treatment of any ailment.

The second primary excitatory chemical, histamine, is a vital inflammatory chemical that indicates not only excess electricity, but high inflammation in the brain and the body. The release of histamine is also a primary indication of several allergic symptoms as it contributes to an inflammatory response and causes constriction of smooth muscle.

It serves as a biomarker that triggers the release of inflammatory markers such as white blood cells and cytokines. Histamine can cause inflammation directly as well as indirectly. When suboptimal, infections can run their course without activation of immune markers to ward of the invasion; however, this primarily occurs with prolonged toxicity.

Dopamine is an excitatory neurotransmitter. When dopamine is released from the brain's storage units, it increases electrical energy in brain neurons. Dopamine is considered our "happy brain chemical" because it activates our brain's reward center, the nucleus accumbens. Our nucleus accumbens serves as our pleasure center, hunger center, and sex drive center.

Dopamine deficiency often causes depression, obesity, and inability to achieve orgasm. Dopamine deficiency also causes diminished cognitive function and fatigue. When elevated, the brain is susceptible to excess electrical voltage which can contribute to a variety of symptoms including anxiety, restless leg syndrome, and fear of public speaking.

Norepinephrine acts as both a hormone and neurotransmitter, and is synthesized from dopamine. It's also known as noradrenaline and along with epinephrine are responsible for the body's fight or flight response, increasing heart rate, and increasing blood flow.

When elevated, it also plays a vital role in increasing blood pressure. If prolonged elevation occurs, epinephrine can begin to decrease and lead to additional symptoms. When suppressed, due to prolonged elevation from toxins, pathogens, and stress, chronic fatigue and depression can ensue.

In addition to norepinephrine, epinephrine is one of our primary excitatory chemicals. More commonly known as adrenaline, epinephrine is a hormone just like norepinephrine. Increases in epinephrine due to toxins and pathogens as well as emotions such as anger or fear can promote epinephrine release which causes increases in blood pressure and heart rate.

This causes the brain to become more electrified and overactive which makes it more susceptible to incoming pain signals. Prolonged elevation as well as prolonged toxicity can lead to epinephrine suppression which can lead to chronic fatigue and depression.

GABA is the brain's primary inhibitory (calming) neurotransmitter; therefore, when released, it helps to calm electrical activity in the brain. When glutamate rises, GABA attempts to correct the elevation in electricity by increasing its release. However, with prolonged elevation of glutamate, GABA production becomes exhausted thus interfering with the natural balancing mechanism for the brain's electricity. GABA's depletion causes anxiety and insomnia.

Serotonin is one of the brain's most potent inhibitory (calming) neurotransmitters. As with GABA, when serotonin is released it helps to calm the brain and decrease electrical activity. Similarly, as the brain becomes electrified, the brain uses more serotonin; therefore, with a prolonged increase in electrical voltage, the serotonin storage units become depleted much quicker.

This depletion results in anxiety, depression, and insomnia. Since the GABA level is extremely difficult to increase directly, serotonin enhancement (through biochemical intermediates) becomes vital in treatment for these ailments.

Because of GABA's difficulty in increasing the level to an acceptable range, the brain needs supplementation to help restore electrical activity. As with serotonin, taurine is easily supplemented as in binds to many positive cations such as magnesium and calcium.

Magnesium is the best choice because it serves an additional purpose to prevent calcium influx into the cell and thus decreasing electrical activity. Taurine also serves as one of the heart's primary amino acids. Suppressed taurine leads to anxiety and insomnia.

The second topic of discussion for acquired abnormalities is hormone imbalance. "Hormone Imbalance" refers to hormones either above or below the optimal functioning level. Optimal is different for every individual; however, hormones are expected to change following the initial Phase of treatment. Hormones must be optimal to help calm the brain through significant modulation of neurotransmitters.

Males and females share a commonality in that acquired ailments such as toxins and pathogens play a similar role in the suppression or imbalance of hormones. Although nearly all hormones are present and display crucial roles in both sexes, their relative quantities in specific hormones differ tremendously. Many hormones act as additional messengers sent to help activate neurotransmitters which control the electrical voltage in the brain.

It's necessary to recognize the importance of; not only direct supplementation of neurotransmitters (through biochemical intermediates), but the restoration of hormones to their optimal levels must occur. Without this imperative optimal hormonal balancing, even adequate neurotransmitters cannot restore electrical current in the brain and body due to poor receptivity.

If receptivity becomes compromised, then the receptors shut down, not allowing the neurotransmitters to activate the appropriate receptor to balance electrical activity in the brain (widely seen in the estradiol-dopamine and estradiol-serotonin connections).

As aforementioned, toxin or pathogen induced hormonal imbalance (suppression) causes hormones to become compromised; however, in addition to this suppression, the female brain naturally begins to lose hormone production regardless of the presence of toxins during peri-menopausal and menopausal states.

The key is not only restoring hormones to their optimal level, but to address the causality of why they became compromised in the first place, whether its induced naturally or unnaturally. Once these causes are identified, hormone treatment can ensue.

If induced unnaturally through contact with toxins and pathogens, Phase 1 of treatment typically restores the hormones to optimal levels without any supplementation. Hormones must be tested before treatment and after Phase 1 to see whether or not hormone supplementation is necessary.

The similarities and differences between male and female hormones along with their associated ailments due to hormone imbalance will be discussed below.

Women have more primary sex hormones involved in the brain's electrical activity and are thus affected more by changes and suppression. The female sex hormones include estrogen, progesterone, and testosterone. All three play a powerful role in modulating the brain's electrical activity.

Two female hormones; estrogen and progesterone, oppose each other with their electrical effect on the brain. Estrogen and testosterone increase electrical activity in the brain while progesterone decreases the brain's electrical activity through their direct role in helping modulate excitatory and inhibitory neurotransmitters.

When women suffer an imbalance of these three hormones, they often experience symptoms of an overactive brain which include anxiety and insomnia, and even changes in cognitive and perceptual functioning. Hormonal imbalance is actually one of the primary reasons women begin to experience these disorders during midlife.

Female hormones control the activity of three brain neurotransmitters; dopamine, serotonin, and gamma-aminobutyric acid (GABA). These three neurotransmitters control much of the brain's electrical activity and are considered to play a primary role in modulating mood.

Dopamine is an excitatory neurotransmitter. In addition it is directly involved in the nucleus accumbens, which is the pleasure center of the brain.

Estradiol, the most potent of the three estrogen hormones, increases dopamine activity in the brain by enhancing dopamine production and by preventing the metabolism (breakdown) of dopamine.

Testosterone, in both sexes, enhances the dopamine receptor which allows for dopamine to activate its receptors in the brain. Therefore, women who suffer testosterone deficiency can suffer from depression and chronic fatigue.

Since the reward center is now underactive due to suppressed dopamine, many women (and men) exhibit symptoms of depression which include loss of motivation, hopelessness, and the inability to get excited. Events that normally triggered happiness and elation now seem dull and uneventful.

Many find it difficult to get out of bed in the morning, while losing interest in activities such as exercise and even going to work every day. Some studies indicate that without optimal hormone levels, cognitive function can even become impaired.

Serotonin is one of the brain's most potent inhibitory neurotransmitters. In the female brain, serotonin cannot activate brain receptors without adequate estradiol. When estradiol levels fall below a certain level (usually below 60-80 pg/dL), serotonin receptors close and become unavailable for serotonin activation.

Without adequeate serotonin, many will begin to lose sleep and gain symptoms of anxiety. Along with GABA deficiency, individuals with compromised serotonin, will lie awake at night worrying about the next day, restlessly thinking about money, work, and intricate detailed plans for the upcoming days. Thoughts press forward with each scenario, good and bad, being played out in their mind, regardless of how likely or unlikely the outcome may be.

Balancing these two neurotransmitters (GABA and serotonin) in addition to taurine, is crucial in restoring electrical activity and calming the voltage in the brain.

GABA is the brain's primary inhibitory neurotransmitter. In fact, drugs like Xanax activate the brain's GABA receptors, and are widely misused to treat anxiety and insomnia disorders associated with GABA deficiency. The female hormone, progesterone is a woman's natural GABA because progesterone converts to allopregnanolone which activates the GABA receptor, thus calming the brain.

As aforementioned, there are many symptoms associated with GABA and serotonin deficiency. It is crucial to balance these chemicals in order to alleviate restless thoughts and unprovoked anxiety. In addition, GABA plays a vital role in balancing glutamate, the brain's number one excitatory chemical, which in excess will cause cell apoptosis and lead to neurological injury through oxidative stress pathways.

When discussing the electrical effect that female hormones have on the brain, the key concept is the ratio of estradiol to progesterone. The excitatory or stimulating electrical effect of estradiol must be counter balanced by the calming effect of progesterone if there is to be harmony in a woman's brain.

Estradiol is a stimulating hormone, which increases dopamine activity in the brain. Because of this increased dopamine it also causes an increase of electrical current throughout the brain.

The second primary female hormone, progesterone, naturally converts to allopregnanolone which activates one of the brain's calming receptors, the GABA receptor.

Women normally begin experiencing premenopausal symptoms in their early forties, approximately 7-9 years before they develop full menopause. During the pre-menopausal years, progesterone production continues to fall while estrogen production remains constant. Without the calming effect of progesterone to oppose the stimulating electrical effect of estradiol, these women begin to suffer the results of an overactive brain which manifests into symptoms of anxiety and insomnia.

As women progress further into their peri-menopause years, progesterone production continues to fall until it reaches post-menopausal levels. During the period of peri-menopause, women often experience symptoms of an overactive brain which includes anxiety, depression, and insomnia.

Unfortunately, when these women seek medical assistance for their new onset of symptoms, they are often misdiagnosed by doctors who remain unaware of the female hormone—brain chemistry connection. Doctors often treat the symptoms of hormonal imbalance such as anxiety and insomnia with addicting drugs like Xanax, Klonopin and Ambien.

In addition, some women who develop progesterone deficiency as they approach their forties, often use alcohol to relax their brain. Alcohol activates the GABA receptor just as the hormone progesterone; therefore serving as a direct substitute for the new onset of symptoms. Prior to their peri-menopausal years, wine was merely consumed socially; however, alcohol now becomes an act of self-medication.

As women progress through peri-menopause towards full menopause, estradiol becomes compromised. Full menopause occurs when the ovaries shutdown and fail to produce both progesterone and estrogen.

As previously discussed, the calming effect of progesterone is seen on the brain's most potent inhibitory neurotransmitter, GABA, which acts to reduce electrical activity in the brain. In full menopause, with the addition of estradiol dropout, the female brain loses yet another potent inhibitory chemical; serotonin. Females can actually record normal serotonin levels; however, suboptimal estradiol levels causes the serotonin receptors to close and thus women suffer from an overactive emotional center of the brain.

Additionally, without adequate estradiol, dopamine production becomes compromised, thus causing the symptoms of an overactive brain to become largely exasperated. See the peri-menopausal sections of GABA and Serotonin and Female Hormones for more information on these effects.

As previously noted, the electrical effect that female hormones have on the brain is primarily the result of the ratio of estradiol to progesterone. The excitatory or stimulating electrical effect of estradiol must be counter balanced by the calming effect of progesterone, if there is to be balance in a woman's brain. Without both of these chemicals, the female brain begins to shut down as multiple neurotransmitter production becomes severely compromised.

These hormonal imbalances and suppressions arise primarily due to toxin-induced suppression which allows for subsequent secondary causalities such as pathogenic infection, hormone imbalance, and changes in Brain Chemistry.

Many physicians fail to recognize that testosterone is a crucial hormone for both males and females. Although present in larger quantities in men, testosterone plays a vital role in dopamine production in the brain for every individual. Without dopamine, the brain's PFC, executive center of the brain, and the nucleus accumbens, the pleasure center of the brain, will begin to shut down. Testosterone deficiency down regulates activity in the brain causing depression and also increased sensitivity to incoming pain signals. In men, the lack of motivation and pleasure become evident.

Pregnenolone is a vital hormone in its crucial role in the production of many sex hormones. Many are familiar with cholesterol and its role in hormone production, but many are unaware that cholesterol converts to pregnenolone which then converts to other sex hormones such as progesterone, estrogens, DHEA, and more. It's essential to keep this hormone at optimal levels for the healthy production of hormones.

Dehydroepiandrosterone (DHEA) is widely known for its use in testosterone enhancement; however, it is actually a natural endorphin which helps enhance the brain's pleasure center. Thus, DHEA can help decrease sensitivity to incoming pain signals by decreasing electrical current in the brain. According to the Journal of Medicine in Thailand, DHEA is considered the "fountain of youth" and can "improve the quality of life".

Additionally, DHEA serves as a potent anti-inflammatory which has been widely used to treat chronic inflammatory conditions such as arthritis; however, since a potent inflammatory marker (TNF-α), prevents the conversion of DHEA-sulfate (DHEA-s) to DHEA, the immune system must be optimized prior to any supplementation including DHEA.

DHEA has also been shown to play a "crucial role" in the development of diseases such as Alzheimer's, heart disease, and some types of cancer. The brain uses an abundant amount of DHEA and its potent anti-inflammatory properties also help increase the production of immune markers such as white blood cells and natural killer cells that help defend against infection. DHEA supplementation should be used in both male and females, however only when quantitative tests reveal its deficiency.

You may have heard of melanocyte stimulating hormone (MSH) in regards to skin pigmentation; however it has many other functions including its association with modulating nitric oxide, inflammation defense mechanisms, and many hormones including anti-diuretic hormone (ADH), Prolactin, luteinizing hormone (LH), and some sex hormones].

In addition to modulating nearly all hormones, MSH is responsible for the manufacturing of endorphins as well as primary immune system modulators. Suppression of this hormone has vast consequences, not only in the production of other hormones and resulting neurotransmitters, but could also inhibit the ability of this immune system marker to signal inflammation and infection in the body. It is obvious to recognize when someone is sick due to the paleness of their skin; however, many are unaware that this directly correlates to MSH and immediately indicates toxin overload.

The thyroid hormone helps to activate dopamine as well as norepinephrine (eventually epinephrine) throughout the brain and body. Any imbalance can cause a multitude of ailments. If the thyroid becomes too high (hyperthyroidism), one can experience symptoms of an overactive brain due to excess electricity from elevated excitatory neurotransmitters. If underactive (hypothyroidism), many neurotransmitters and resulting cells cannot activate, thus causing symptoms of an underactive brain. People who suffer from hypothyroidism can experience chronic fatigue, depression, and find it extremely difficult to lose weight even when on a scheduled diet and exercise routine.

Additionally, the thyroid is associated with body temperature; therefore, a decreased thyroid will cause the hands and feet to become cold. Many feel the need to wear sweatshirts and additional clothing even when the temperature is 75 or 80 degrees Fahrenheit. Although it affects both men and women of all ages, everyone has a Grandmother who is dressed nearly from head to toe in the middle of July.

After genetics are addressed or identified, only treatment of acquired abnormalities such as toxins and pathogens can alleviate said health ailments.

Numerous studies have proven that in order to allow pathogens into one's system, the immune system must be compromised at some point to allow entry. The most common immune suppressant that individuals come into contact with is mycotoxins. These mycotoxins enter the body through its most potent route of inhalation, and with positive HLA-DRB-DBQ genetics, they are readily stored.

The body's natural defense system begins to shut down upon entry of said toxins. Without excretion of these toxins, the immune system stays in a compromised state, allowing for entry of unwanted bacteria and pathogens such as Lyme disease, *babesia*, and *bartonella*. The latest scientific research shows that Lyme can affect the brain as well as the body.

Many are unaware of the parasitic infection as only 10% of infected Lyme disease patients receive the classic "bullseye" rash. Additionally, many do not even recall the tick bite or attachment whatsoever (fewer than 50%).

Doctors readily prescribe antibiotics to treat pathogens such as Lyme disease (as with most common infections); however, if not caught within the first two weeks, antibiotics are not only useless but extremely dangerous (antibiotics can successfully eradicate Lyme within two weeks of entry). Since most are unaware of the infection, and the majority do not seek treatment within the first two weeks of entry, most infected patients require a different Lyme treatment altogether.

Many are concerned with eradicating these pathogens and treating Lyme disease; however, many of the associated ailments can be treated first without ever attacking the pathogens directly. For most patients full eradication is not necessary and may not ever have to be addressed in order to restore one's health.

Through implementation of the method and system of the present invention most people see a dramatic improvement in their health without ever attempting to eradicate these pathogens and treating their Lyme disease. The true problem lies in correcting all the damages due to the misdiagnosed and mismanaged treatments provided by physicians who are unaware of the latest science behind these infections.

Nearly 80% of all infectious disease builds a biofilm. A biofilm is a polysaccharide extracellular matrix that forms when a fluid is flowing past a solid. Common biofilms include dental plaque and the matrices that form around medical implant; however most physicians are unaware of the infectious disease connection to biofilms.

You can think of a biofilm as the "fort" or "shields" that pathogens build in order to survive on their host. As these pathogens begin to enter the bloodstream, they flow against the side walls of the capillaries, veins, and arteries. 99% of all bacteria do not want to flow; they prefer to be at rest which leads to the production of biofilm.

There is a misconception that only pathogens like Lyme or *bartonella* build biofilms; however, toxins such as mycotoxins and *candida* build them as well. The more species present in the body, the more difficult the biofilm becomes to penetrate. Biofilms must be penetrated in order to release and attack the hiding pathogens directly.

Without direct contact with the infectious disease, these bugs will continue to build, and are completely free from our own immune system. In fact, our immune system recognizes these biofilms as invaders and sends macrophages to attack the unwanted invader; however our body's defense system is useless and can actually cause macrophage-induced death surrounding the biofilm causing more harm to the brain and body.

The most common treatment is to prescribe antibiotics; however, according to the American Association of Quantum Medicine and The University of California at Berkeley, antibiotics cannot fully penetrate the biofilm causing their administration to be useless and dangerous. Additionally, biofilms are nearly 1000 times more resistant to antibiotics when compared to "free flowing" bacteria.

Additionally, biofilms, as any living organism, do not want to be killed and do everything they can to prevent this including adapting and becoming even more resistant to antibiotic therapy. Antibiotics are only effective when in direct contact with bacterial and pathogenic infections, and this is not the case in any biofilm producing diseases.

Since biofilms use their host for energy, it is common for physicians to "starve the biofilm" from its primary nutrients (such as magnesium) by not supplying the body what it requires especially in a time of need. As aforementioned, biofilms are quite adaptable and this does not help eradicate them at all.

Biofilm detachment is a natural cycle among any biofilm producing specie. However, in terms of survival, the biofilm can detach from its current location and reattach elsewhere where it can find what it needs to survive. Therefore, not only does this not help eradicate the biofilm, it causes the biofilm to spread faster. This treatment harms the body by robbing the body of precious nutrients in addition to causing the biofilm to extend.

The gut-brain connection is now well-established in the scientific community. When pathogens like Lyme disease infect the body, they begin to attack the gut lining. Without the lining in the gut, absorption of vital nutrients becomes extremely compromised. Additionally, pathogens and nutrients begin to leak through the lining and into the bloodstream.

As the unwanted materials begin to pile up in the blood stream, antibodies in the immune system identify them as invaders and begin to attack these materials. Also, toxins begin to move towards to the brain causing changes in brain chemistry.

Neurotransmitters in the brain respond by increasing action potentials in the cell causing excess electricity to run throughout the brain and body. The primary neurotransmitters affected by pathogens include glutamate, histamine, norepinephrine, and epinephrine. As glutamate elevates it causes calcium influx into the cell. Calcium mediates the voltage sent throughout each cell and thus the entire body.

With too much glutamate caused by toxins and pathogens massive bursts of electricity are continually sent through the brain and body causes the entire system to become overactive.

Figure 3:
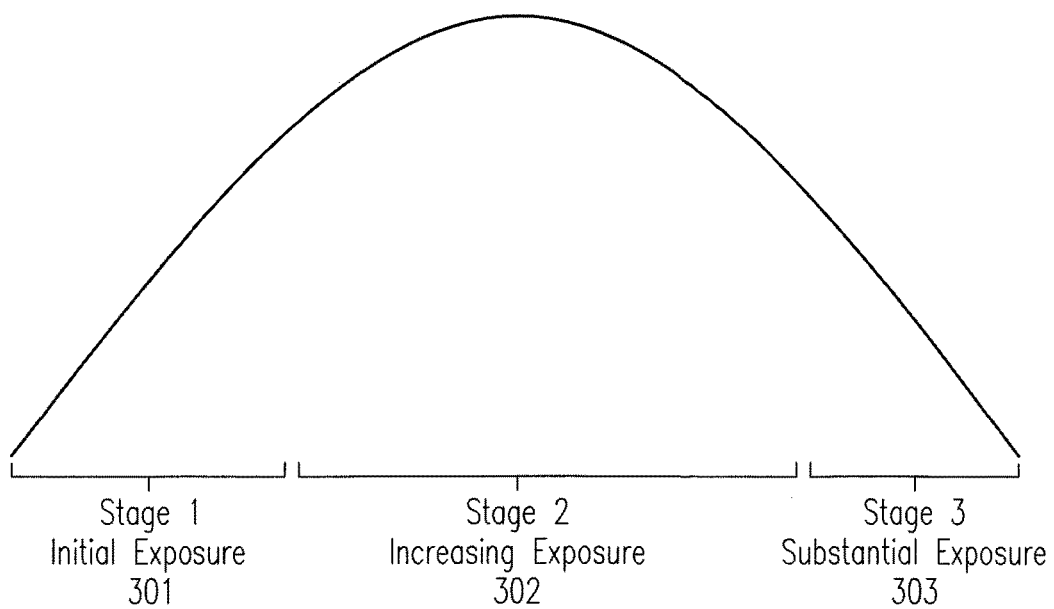
FIG. 3 is a graph illustrating general trends of neurotransmitters over increasing exposure to toxins and pathogens.

As electricity increases; inhibitory chemicals increase in attempts to balance this new onset of increased electricity. Serotonin and taurine rise, in addition to GABA, in an attempt to balance the glutamate and histamine (excitatory) excess, as illustrated in FIG. 3.

Associated symptoms of an overactive brain include anxiety, chronic pain, fibromyalgia, and insomnia. The increased histamine causes the joints to swell, causing joint pain. This pain can be localized or spread throughout the body (usually termed fibromyalgia).

As the blood becomes clogged with biofilm producing species, the capillaries and other blood transport mechanisms become compromised. As the clotting and clogging persists, these transport mechanisms become compromised as predicted by Fluid Dynamic concepts in engineering which predict changes in pressure, volumetric flow rate, frictional forces, and velocities around clogged areas.

This readily causes contractions which result in headaches, migraine, and increases in blood pressure and heart rate. Pathogens like *babesia* crawl inside the red blood cells (as with Malaria) causing the cell to expand making it even more difficult to keep blood pressure and heart rate under control. Red blood cells are typically 7-8 microns in diameter, and blood capillaries can be as small as three microns in some places. As infections crawl into the cell it causes the cell to bloat which provide a mechanism for these symptoms as it become more difficult to travel within the capillaries.

Additionally, if these pathogens are left untreated they begin to attack the brain's protective shield, the myelin sheath. This causes a wide variety of neurological problems ranging from chronic pain and migraines to diseases such as Alzheimer's and Multiple Sclerosis. As previously discussed, the brain is an electrical organ. It relies on neurons to "jump" from synapse to synapse to relay messages throughout the brain and onwards to the rest of the body. The electrical insulation is the myelin sheath and is vital in order to go from synapse to synapse.

As the myelin sheath becomes damaged, communication among neurons is slowed dramatically resulting in serious mobility and pain complications and even neurodegenerative diseases such as Alzheimer's disease.

As aforementioned toxins shut down the immune system allowing entry of unwanted pathogens such as Lyme disease. Additionally, these toxins suppress the hormones causing many ailments in the brain and body. Pathogens play a similar role in causing an imbalance in the hormones; however, their potency is less than that of mycotoxins. Nevertheless, their effect is seen and must be addressed if it persists through the first two Phases of treatment.

A Herxheimer reaction (HX) is seen when attacking any pathogen or bacteria in the body and is exemplified when attacking biofilm producing species. An HX occurs when the toxins are released from these pathogens causing unwanted increases in toxicity and thus raising electricity throughout the body. This effect must be minimized, and in order to achieve this, toxins must be removed first.

In addition the body and brain must be calmed and its nutrition replenished, as well as toxin removal. These three entities can be accomplished through one feat, an intravenous drip.

The IV drip must be administered prior to attempts of treating any pathogen as many will see their hormones restored to optimal levels without ever addressing their Lyme disease or any other infection. Hormonal therapy can still be effective with pathogens present in the body; however, with toxins present, this is nearly impossible to achieve.

70% of the body's immune system is located in the gut. As the gut becomes compromised due to onslaught of pathogens in addition to their common method of treatment for eradication (antibiotics), many individuals infected with pathogens such as Lyme disease suffer further due to overprescribed antibiotic treatment.

Intestinal dysbiosis is the term used to describe an imbalance of intestinal flora (organisms). Since the mechanism action of antibiotics is to stop the production of all cells, beneficial or toxic, in attempts to eradicate the infection (hoping the beneficial outweighs the toxic), prolonged antibiotic therapy causes a massive imbalance in the gut's intestinal flora. This treatment kills the good bacteria such as *bifidobacterium* and *lactobacillus* which will cause massive disturbances in the brain and body.

Additionally, as the gut lining is further destroyed through this treatment, the gut begins to lose its natural pH of 1-2 to help breakdown food and bacteria and becomes more basic which further leads to overgrowth of toxic bacteria such as *Klebsiella* and *Proteus*.

These toxic bacteria and elevated pH further destroy the lining causing unwanted bacteria to flow throughout the blood stream. Additionally, as aforementioned, the vast majority of the immune system lies within the gut, and this immune system becomes destroyed when the intestinal flora becomes outweighed by toxic bacteria and unwanted *candida* overgrowth.

The gut may be addressed only if necessary after environmental toxins, nutrition, the brain, and hormones have been addressed first in Phase 1 and Phase 2.

As aforementioned, timely administration is the key concept to healing. Additionally, conventional medicine relies primarily on subjective cues and little amount of objective analysis to diagnosis any ailments. The method and system of the present invention relies heavily on non-invasive quantitative data performed on neurotransmitters profiles, blood and hormonal testing, biofilm assays, amino acids and toxicity profiles. As all other sciences are based primarily on factual objective data, it is the stance of the method and system of the present invention to do the same.

Although there are numerous quantitative profiles necessary for proper diagnostics, medicine does not treat numbers—it treats patients. Once the patient feels better and their primary ailments have been addressed and alleviated 205, treatment should stop 206.

Figure 2:
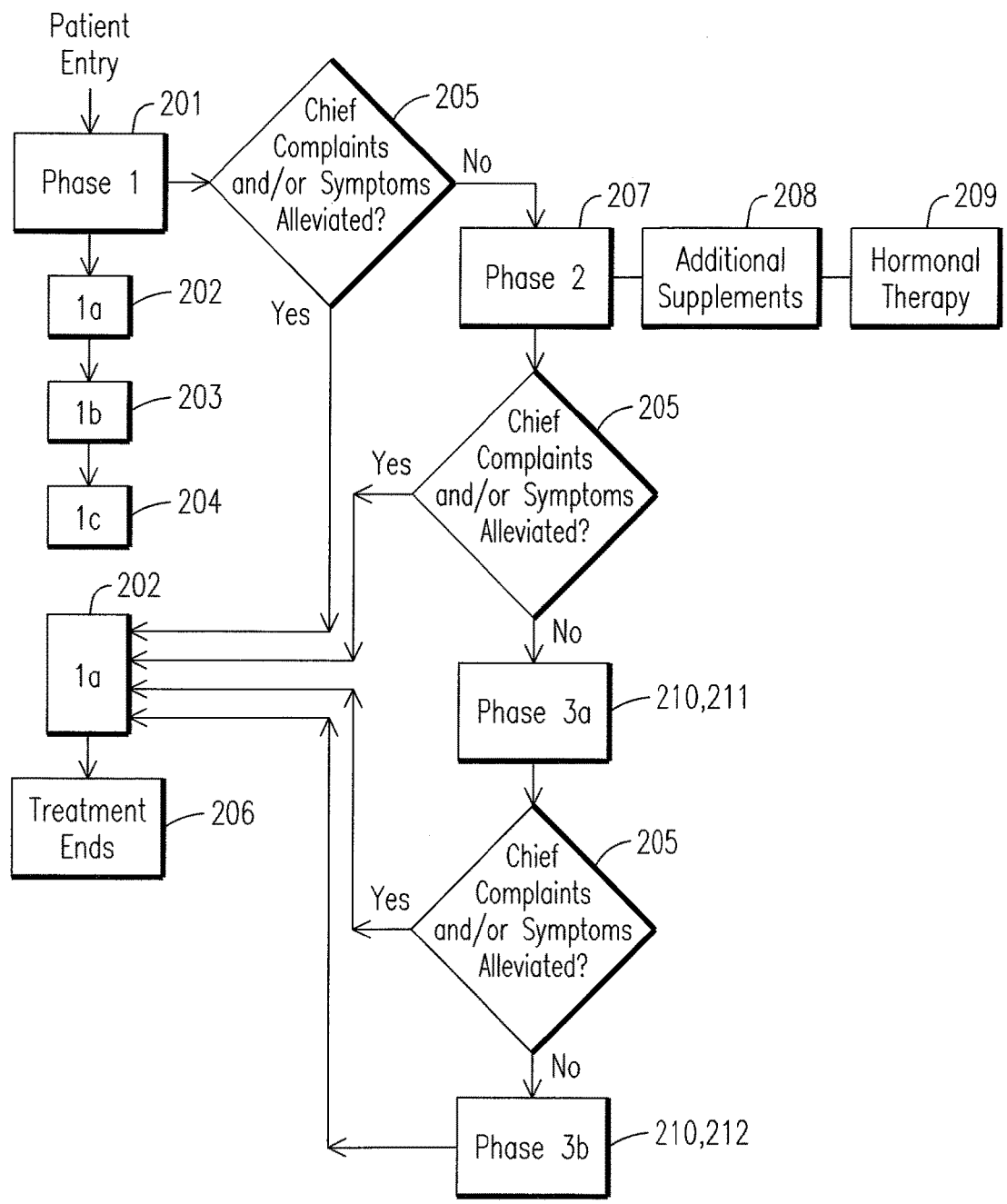
FIG. 2 is a flowchart illustrating the steps for treatment using the method and system of the present invention.

There are three Phases to the method and system of the present invention, as illustrated in FIG. 2, which are outlined in a specific order that must be followed in order to ensure that the treatment not only be effective, but cause no harm to any individual undertaking this protocol. The Phases and the steps that encompass each Phase must be addressed in the following order:

Phase 1—Quantitative Testing and Returning to Baseline 201:
 1a—Quantitative Testing 202
 1b—Test your Home for Mycotoxins 203
 1c—Return to Baseline—Calm the Brain, Remove Toxins, Replenish Nutrition 204
 Phase 2*—Full optimization 207:
 2a—Additional Supplementation 208
 2b—Hormonal Therapy 209
 Phase 3*—Eradication 210
 3a—Gut Therapy 211
 3b—Pathogenic Eradication 212

The outlined order will not change, especially Phase 3, as this is the most dangerous and requires the most time, and it should be addressed last for everybody. Some may think otherwise; however, they do not understand that timely administration of causality is vital. Phase 2 and Phase 3 are marked with an asterisk as they are only necessary if Phase 1 does not alleviate the chief complaints of the patient. However, both Phase 1 and Phase 2 are extremely safe, effective, and timely.

Although it may seem that many ailments can be treated effectively with this protocol, the background information section demonstrates how these ailments are not true diagnoses, they are merely additional symptoms of true underlying causes that have been outlined in detail in previous sections of this invention.

The three Phases of treatment for this invention can be utilized as the primary form of treatment for the following ailments. Refer to the previously outlined section as to why the brain regions depicted below can be treated effectively through Phase 1. Any co-morbidity (combination) of the below ailments can also be treated.

Phase 1 Ailments:
Anxiety, Bipolar II Disorder (BP)**, Chronic Fatigue Syndrome (CFS), Chronic Migraines, Depression, Insomnia, Toxicity*
Anxiety
 Primary—Anterior Cingulate Gyrus System (ACS)
 Secondary—Deep Limbic System (DLS)
 Tertiary—Prefrontal Cortex (PFC), nucleus accumbens (NA)
BP
 Primary—ACS, DLS, NA, PFC
CFS
 Primary—NA, PFC
 Secondary—DLS, ACS
Chronic Migraines
 Primary—ACS, DLS
 Secondary—NA
 Tertiary—PFC
Depression
 Primary—DLS, PFC, NA
 Secondary—ACS
Insomnia
 Primary—ACS, DLS
 Secondary—PFC, NA
Toxicity affects all brain regions
Phase 2 Ailments:
Any ailment persisting through Phase 1, Fibromyalgia, Idiopathic Seizures (IS)**, Fibromyalgia
 Primary—ACS, DLS
 Secondary—NA, PFC
IS
 Primary—ACS, DLS
 Secondary—NA, PFC
Phase 3a Ailments:
Any ailment persisting through Phase 2, Irritable Bowel Syndrome (IBS)
IBS
 Primary—ACS, DLS
 Secondary—NA, PFC
Phase 3b Ailments:
Anything persisting from Phase 3a, Pathogenic Infections*
Pathogenic Infection affects all brain regions

*Toxicity and Pathogenic Infections refer to the previously outlined definitions throughout this invention. Persisting infections such as urinary tract infections and tonsillitis can also be effectively treated through the 3 Phases of treatment.

**BP refers to any sudden onset of "diagnosis" of bipolar II disorder which tends to "develop" around age 18—not intended to be primary form of treatment for true genetic bipolar I or schizophrenia

**IS are seizures that have no "easily discernable" causality—i.e. are not diagnosed through genetics or brain scans or any commonly accepted epileptic/seizure testing—idiopathic is a fancy term for "we do not know what causes your seizures." As previously stated, any co-morbidity (such as bipolar depression) of the above ailments can be diagnosed and treated under this invention This outline applies to the majority of individuals; the method and system of the present invention is designed to give any individual the physical tools necessary to overcome their ailments, thus making any emotional or psychological ailment easier to overcome. Most individuals regain their physical health and alleviate their issues through supplying these physical tools; however in some cases, psychological ailments must be addressed outside the capacity of this invention. Although, many psychological ailments are must easier to address after one has the physical tools they need to overcome these conditions.

As many individuals spend years suffering from their ailments, these ailments begin to dictate their life to a degree. In other words, these conditions become "normal" to said individual. Many need to re-teach their brains and bodies how to live healthy once again. In some cases, the brain and body must be given time to adapt to these newly acquired physical tools.

By no means is this suggesting that everyone can be treated the same; however, the aforementioned outline for Phases of treatment will depict the majority of individuals. Additionally, some ailments require only one Phase, some two, and some all three Phases. The ailments that require more than just the first Phase of treatment will still see improvement when progressing from Phase to Phase; however, it the individuals' chief complaints are still not alleviated, then treatment should persist from Phase 1 onwards to Phase 3. Since this outline applies to the majority of patients, the converse is also true in that some ailments listed in Phase 2 or Phase 3, may also be alleviated in just the first or second Phase.

Phase 1:
 1a. Quantitative Testing
These objective data serves as a guide to pinpoint patterns that coincide with the two diagnostics outlined in previous sections—toxicity and pathogens. All testing outlined henceforth can serve multiple purposes; however, the patterns addressed will primarily serve to show the different stages of toxicity and pathogenic exposure and what each physician should identify as they analyze and tie together each delineated test.

Note: Although any of these tests are not commonly performed at a medical office, Physicians should still not ignore cues that they were already taught regarding any of these tests as the analysis shown is primarily meant to point out the values correlated with toxin and pathogen exposure.

Genetic Testing

As previously outlined, there are many genetic tests that can be performed; however, the most crucial remains HLA-DRB-DBQ. The specific subset that makes individuals susceptible to toxins must be identified in order to proceed with the rest of the quantitative testing. It is a simple blood test, but it must be decoded in accordance with "Mold Warriors."

Neurotransmitter Profile

As outlined in the Brain Chemistry section, neurotransmitters play a vital role in regulating the brain's electricity. Since 1959, urine has been confirmed as an effective and reliable way at revealing one's neurotransmitters. The following will depict trends that each physician utilizing this invention should correlate. Refer to the Brain Chemistry section for background information on the importance on the following neurotransmitters $1^{st}$—Separate the excitatory neurotransmitters and the inhibitory neurotransmitters. "Elevated" will refer to a chemical that is too high for optimal brain performance and voltage while "Suppressed" will refer to a chemical that is too low for optimal brain performance and voltage. "Optimal" refers to the target range for the majority of individuals. Since every individual is unique, some require more or less than others.

Excitatory—listed from highest importance to lowest
    Glutamate* (micromole/gCr)
        Optimal Range—25-35
        Elevated—greater than 50
        Suppressed—less than 18
    Dopamine (microgram/gCr)
        Optimal Range—approximately 125-165
        Elevated—great than 240
        Suppressed—less than 90-100
    Norepinephrine (microgram/gCr)
        Optimal Range—approximately 35-40
        Elevated—greater than 50
        Suppressed—less than 20
    Epinephrine (microgram/gCr)
        Optimal Range—approximately 10-14
        Elevated—greater than 50
        Suppressed—less than 18
    Histamine (microgram/gCr)
        Optimal Range—approximately 25-35
        Elevated—greater than 50
        Suppressed—less than 13-15
    Inhibitory—listed from highest importance to lowest
    Serotonin (microgram/gCr)
        Optimal Range—approximately 400-1000 (as high as 2000 in some individuals)
        Elevated—difficult to assess
        Suppressed—less than 250
    Taurine (micromole/gCr)
        Optimal Range—400-1000 (sometimes higher in some individuals)
        Elevated—difficult to assess
        Suppressed—less than 200
    GABA* (micromole/gCr)
        Optimal Range—6-10
        Elevated—approximately greater than 14
        Suppressed—less than 4
        *Another important correlation is between Glutamate to GABA in which the ratio should be approximately 5:1*
    Other correlations—see next section
    DOPAC—3,4-Dihydroxyphenylacetic acid
    L-DOPA—levodopa
    5-HIAA—5-Hydroxyindoleacetic acid FIG. 3 depicts the general trends of neurotransmitters over increasing exposure to toxins and pathogens. When analyzing neurotransmitters, one first must look for easily discernable trends. Other more in depth analysis is only needed if the following trends cannot be determined.

When the body is initially exposed to toxins and pathogens, it responds by increasing the production of excitatory neurotransmitters. As each of these excitatory neurotransmitters become too electrified, the inhibitory neurotransmitters attempt to counteract the increase in electrical activity by increasing their production.

If both the excitatory and inhibitory neurotransmitters are in the first period of elevation, this signals stage 1, an initial exposure period to toxins and pathogens 301. Stress can produce similar results; however, toxins and pathogens cause these changes at a much more potent and expedited rate.

If the excitatory neurotransmitters are elevated, but the inhibitory neurotransmitters are suppressed, this signals that the individual is in stage 2 of exposure 302 which signals a more prolonged exposure to toxins and pathogens. The excitatory chemicals in this stage are usually extremely elevated which accounts for the trends illustrated in FIG. 3.

If both chemicals are suppressed, this signals a substantial exposure to toxins and pathogens as the brain has literally begin to shut down as seen in stage 3 303. However, this profile must be directly paired with the following test, an amino acid profile.

Amino Acid Profile

As amino acids are the building blocks of proteins and provide many of the precursors to the outlined neurotransmitters, their testing is vital for this protocol. Alone, the neurotransmitter test is useful; however, it becomes more easily correlated when paired directly with the amino acid profile. There are over thirty amino acids that are easily tested through one urine sample; however, only the most important will be outlined. Additionally, there are many uses in the brain and body for these depicted amino acids; however, the most important for diagnostics will be outlined. Again, general trends in this test are used to correlate with other tests to analyze the degree of exposure for the patient (specific values will not be outlined).

Methionine—for its role in preventing oxidative stress as well as in the norepinephrine to epinephrine conversion
    Phenylalanine—for its role in converting to phenylethylamine (PEA), an excitatory chemical
    Cysteine—for its role in the glutathione cycle
    Histidine—for its role in converting to the second most potent excitatory chemical, histamine, shows gut integrity through conversion (discussed later)
    Glutamine—for its role in converting to glutamate, shows gut integrity through conversion (discussed later)
    Aspartate—for its role as an excitatory chemical
    Tyrosine—for its role in the conversion to dopamine
    Serine—for its role in the NMDA receptor which acts with glutamate to allow calcium influx into the cell generating action potentials and thus excess electricity throughout the brain and body Ammonia—elevations seen in increased toxin exposure Tryptophan—for its role in converting to 5-hydroxytryptophan (5-HIP) and eventually serotonin and melatonin Many others have importance, but are depicted above such as Lysine, Leucine, Isoleucine, Valine, Arginine, beta alanine, etc.

Correlations between Neurotransmitters and Amino Acids (1) If the neurotransmitters are elevated and the amino acids are elevated or optimal, this provides additional correlation with the initial exposure stage.

(2) If the neurotransmitters are suppressed and the amino acids are suppressed, this coincides with additional correlation with the substantial exposure stage.

(3) If the neurotransmitters are suppressed and the amino acids are normal or elevated, this signals a conversion problem. A "conversion" problem is a term that encompasses the enzymes and reactions involved in producing neurotransmitters. For example, tyrosine (amino acid) produces L-DOPA through tyrosine hydroxylase which then proceeds to form dopamine. If tyrosine is high, but dopamine is low, this signals an issue with this reaction. This requires supplementation with cofactors (such as Vitamin B6 among many others) involved in said reaction which is addressed in the amino drip in Phase 1 of treatment. Additionally, a conversion problem can be seen when looking at L-DOPA, DOPAC, and 5-L-DOPA converts to dopamine and dopamine is broken down further into one of its primary metabolites, DOPAC. Elevated Dopamine with suppressed DOPAC signals an issue in the metabolism of dopamine through Catechol-O-methyltransferase (COMT) and monoamine oxidase (MAO) enzymes. Since 5-HIAA is a metabolite of serotonin, the same application applies. Additional conversion problems can be seen in the conversion of dopamine to norepinephrine to epinephrine. In all these cases, cofactors, enzymes, etc. must be addressed for each reaction which is simultaneously addressed in the amino drip in Stage 1 of treatment.

(4) In addition, if at any time the amino acids are suppressed, this immediately signals Stage 3—Substantial Exposure, as illustrated in FIG. 3. The increased toxicity has now affected not only the brain, but now the gut integrity as well.

Blood Analysis (Primarily Hormonal Profiles)

Physicians should not ignore things that they were already taught regarding any of these tests as the analysis shown is meant to point out the values correlated with toxin and pathogen exposure. Hormones must be analyzed individually for treatment purposes; however, overall suppression of the hormones combined is a primary indicator of significant exposure to toxins and pathogens. Most will return to optimal levels following Phase 1 of treatment; however, if the patient requires Phase 2, optimal levels will be depicted below. All ranges are approximate, and are primarily used to correlate patterns among all these quantitative data.

Unless specified the following tests are to be performed for both males and females.

Pregnenolone

Levels vary among males and females; but anything less than 25 ng/dL is suppressed. Optimal ranges also vary but a good approximation is about 100 ng/dL (sometimes more is needed).

Progesterone

Levels vary among males and females, but anything less than 0.4 ng/mL is suppressed for both sexes. Optimal ranges for males are approximately 1 ng/mL. A specific number for females is too difficult as they vary tremendously among menstrual cycles.

Testosterone (Free)

Levels for males less than 7-11 pg/mL are considered suppressed. For females anything approximately less than 0.4 pg/mL is suppressed. Optimal levels are approximately 12-20 pg/mL and 1-1.5 pg/mL for males and females respectively.

DHEA (Dehydroepiandrosterone sulfate)

Approximately 350-500 ng/dL is optimal for both male and females, although it varies among the sexes and has been correlated with age. Suppressed is considered less than 150-225 ng/dL.

MSH (alpha melanocyte stimulating hormone)

Levels less than 15 to 17 pg/mL are considered suppressed while approximately 30-35 pg/mL is considered optimal.

ACTH (adrenocorticotropic Hormone)**

ACTH can reveal pituitary function in conjunction with prolactin and IGF-1. As it is a hormone, it also serves as a marker for hormonal suppression. Suppressed levels coincide with less than 20-25 pg/mL while optimal falls in the approximate range of 40-50 pg/mL depending on the individual.

IGF-1 (insulin-like growth factor 1)**

IGF-1 should be used in conjunction with other pituitary hormones as ACTH. Although IGF-1 is correlated with age, approximate optimal ranges for adults should be between 300-400 ng/mL. Anything less than 200 ng/mL is suppressed.

Prolactin**

These ranges vary from male to females, but anything below 5 ng/mL is suppressed for both sexes.

**These 3 pituitary hormones need to be analyzed separately as well to address the low chance possibility of a pituitary adenoma. If all hormones are suppressed while one putiutary hormone is substaintially elevated (i.e. IGF-1 greater than 800 ng/mL), additional measures need to take place (i.e. MRI and referral)

Vitamin $D_3$ (25 OH Vitamin D)

Vitamin D has a variety of uses throughout the brain and body; however, suppression is indicative of significant toxin exposure. Suppression is less than 45 ng/mL. Optimal is preferably 70 ng/mL and above.

CMP (Complete Metabolic Panel)

Protein levels less than 7 g/dL are an indication of poor absorption which will correlate with the amino acids and neurotransmitters. If low, this can also indicate a high carbohydrate and sugar diet which is another indicator of poor absorption as the body craves for foods with high energy sources such as carbohydrates and sugars. Optimal is 8-8.2 g/dL.

A/G Ratio

The A/G ratio (albumin to globulin ratio) can indicate excessive clotting throughout the body which should be correlated with Fibrinogen, the body's primary clotting factor. If clotting is high this can show significant exposure to toxins and pathogens. Elevated is greater than 2.5 and optimal is 2.

AST and ALT

AST and ALT (alanine transaminase andaspartate transaminaserespectively) are liver enzymes that must be performed in order to administer the amino drip of Phase 1. Since toxins are processed through the liver, elevated liver enzymes can show significant toxin exposure. Elevated AST greater than 35 U/L and elevated ALT is greater than 50 U/L.

Carbon Dioxide

Carbon dioxide can be an indication of the body's pH as well as the effectiveness of oxygen exchange. If elevated (great than 30 mmol/L) it is a sign of mycotoxins that are lining the bottom of the lung cavity. This can result in a patient complaining of inability to catch their breath, although SPO$_2$ indications are normal (~99%).

CBC w/differential (Complete Blood Count)

Many individual white blood cells (WBC) can show a variety of abnormalities; however, this invention serves as a guide to show the severity of the two main diagnoses—toxins and pathogens. The red (RBC) and white blood cells along with platelets can show this severity.

For pathogens, initial infections will show an increase in WBC while significant exposure to either pathogens and/or toxins will show suppression in the total WBC count (approximately less than 7000/uL). Although many are taught that significant suppression of WBCs can indicate entities such as leukemia, significant toxin exposure can show similar results.

Significant exposure can also show anemic conditions in the RBCs (suppression). Additionally, the RDW (red blood cell distribution width) can show if a pathogen such as *babesia* has entered the RBCs (greater than 16%). Suppression of the WBCs will correlate directly with likely suppression of neurotransmitter and amino acid profiles.

G6PD (Glucose-6-phosphate dehydrogenase deficiency)

This must be accounted for in all individuals due to the use of many vitamins, amino acids, and minerals in the Phase 1 IV drip for Phase 1 (including Vitamin C)

Estradiol—female only

For females, Estradiol must be at least 60 pg/mL as the serotonin receptors will close if not adequate. For ovulating females, Below (60 pg/mL) is suppressed while approximately 70 pg/mL or above is optimal depending on various factors such as the Phase of the menstrual cycle at the time of the test.

Estrone*

This can be used to coincide with the other hormones; however, elevated levels in males (>greater than 65 pg/mL) can be a sign of more significant problems such as prostate cancer.

PSA*—male only

This is used for safety concerns such as prostate cancer.

*Not for diagnostic purposes, only to ensure health of patient as elevated PSA and Estrone in males can indicate various forms of cancer such as prostate cancer.*

Other tests may be performed throughout the method and system of the present invention at the discretion of the physician. Some of these tests are depicted in the initial testing for Phase 2. Before beginning Phase 2, additional testing is required to perform a full optimization. Some of these tests will include TSH (thyroid stimulating hormone), ADH (anti-diuretic hormone), FSH (follicle-stimulating hormone), LH (luteinizing hormone), ferritin, Free triiodothyronine, Free thyroxine, C-Reactive Protein, Thrombin-Antithrombin Complex, CD4:CD8 ratio, MMP-9, Immunoglobins Quantitative, various infectious disease (Lyme-Western, etc—prior to Phase 3b), various vitamins and minerals (B12, B6, selenium, etc.), and fibrinogen and more can be addressed if necessary as many tests are already required and the patient's well-being is the main concern thus a minimal amount of tests are depicted for Phase 1 of treatment.

Optimal and suppressed ranges may vary between individuals and are only approximate values to depict trends.

Mycotoxin Profile

As there are only two sources of acquired abnormalities, and the majority of the aforementioned testing is to diagnose and correlate the amount of exposure to toxins and pathogens, it comes to no surprise that a mycotoxin profile must be administered. If the pattern of hormonal, amino acid, and neurotransmitter profiles depict suppression, it will come to no surprise that mycotoxins will be present in one's system. Although there are an abundance of mycotoxins that all affect the human brain and body, 3 are common and have generated preexisting testing and are required through this invention.

Aflatoxin

Anything over 2 ppb are considered elevated. Optimal values are as close to zero as possible.

Ochratoxin

Levels over 3 ppb are considered elevated. Optimal values are as close to zero as possible Trichothecene Trichothecene is by far the most potent of the mycotoxins and must be as close to zero as possible. Anything over 0.2 ppb is considered elevated.

It is worth noting that the biofilm can hold these toxins as well; therefore, this test will usually indicate the minimal amount within the body as it only tests for "free flowing" mycotoxins.

1b—Test your Home for Mycotoxins (Spores)

After the toxin susceptibility has been identified or ruled out, a home mold spore test must be performed (mycotoxin testing preferred, although availability is limited). The reason this is encompassed in this invention is because the treatment protocol relies on treating true underlying causes. After inherited abnormalities are pinpointed (Genetic Testing), acquired abnormalities can only trace back to two sources—toxins and pathogens. Thus, even after all the diagnostics and treatment that can be executed through this invention, preventing problems from reoccurring it vital to long term success. This proves to be nearly impossible if all the removed toxins are implemented once again into the brain and body through exposure of the home upon completion of the method and system of the present invention.

1c—Return to Baseline—Calm the Brain, Remove Toxins, Replenish Nutrition

The following is considered a "Phase 1 IV drip" for the patients and should be administered back to back starting on Monday two-3 times per week for two-4 weeks. The majority of patient's symptoms will be alleviated through Phase 1 of treatment. It should be administered for 60-120 minutes depending on the dosages employed. On the "off" days, the days in which intravenous therapy is not being administered, the following oral supplements should be taken:

5-hydroxytryptophn (5-HTP)—200-1000 mg-1 hour before bedtime

Magnesium Taurate—400-1200 mg-1 hour before bedtime

Cellgevity—2-4 capsules per day
if 2 capsules—2 capsules 1 hour before bedtime
if 4 capsules—2 capsules 1 hour before bedtime and 2 capsules after breakfast in the morning The following is the intravenous formula for the Phase 1 IV drip:

Vitamins 1000 mcg-3000 mcg of hydroxocobalamin (B12)—1000 mcg starting point 75-200 mg Pyridoxine hydrochloride (B6) can go to around 400-600 mg-100-150 mg starting point 140-400 mg Dexpanthenol (B5)—200-250 mg starting point B Complex 100 (1-2 mL) which contains the ingredients listed below
  Thiamine Hydrochloride 100 mg, Riboflavin 5' Phosphate Sodium 2 mg, Pyridoxine Hydrochloride 2 mg, Dexpanthenol 2 mg, Niacinamide 100 mg 500-2000 mg Vitamin C (ascorbic acid)
Minerals
0.5 mg Manganese
2 mg Zinc
10 mcg Chromium
60-300 mcg Selenium up to 1000-4000 mcg but should be discontinued after two weeks
100-800 mg Magnesium—30% bound to albumin—100-300 mg
Amino Acids
L-Taurine—150-600 mg
L-Tryptophan—20-75 mg
L-Glutathione—400-1800 mg
L-Methionine—25-75 mg
N-Acetyl—Cysteine (NAC)—50-250 mg
L-Theanine—20-60 mg For any of the ailments treated in this invention, other entities can be added in accordance with all the outlined quantitative data as well as prior experience.
  These additional ingredients include:
  50-350 mg L-Arginine
  50-200 mg L-Lysine
  25-75 mg Lipoic Acid After Phase 1 is complete, the quantitative testing will be repeated to ensure optimal levels have been reached. However, if the chief complaints of the patient have been alleviated than the patient has completed treatment even if all values are not optimal.

The maximum dosage should not be employed for all ingredients simultaneously, and the maximum dosage should only be employed for 1-2 ingredients with the others remaining toward the middle range. The middle range is usually the optimal dosage for each patient. For example, a range of 50-100 mg, the middle range would be 75 mg. Furthermore, the first drip for each patient should be on the lower range of each ingredient to ensure a smooth outcome. For the same example, the lower range would be 50-60 mg.

Phase 2—Full Optimization:

This Phase implies correcting any imbalance without attempts of eradication. Hormonal optimization and supplementation with bio-identical hormone replacement therapy (BHRT) is only needed if hormones do not return to optimal levels following Phase 1. Additionally, if chief complaints persist through Phase 1, then Phase 2 will serve as the next stage of treatment in this invention. Phase 2a can include additional supplementation such as a probiotic, fish oil, S-Adenosyl methionine (SAM-e), among others that corresponds to the quantitative testing (amino acids, hormones, neurotransmitters, etc.) as well as prior experience of the brain and body As aforementioned, if BHRT is to take place then more tests are needed as mentioned in the above sections.

Quantitative testing of the neurotransmitters and hormonal assays should be repeated to ensure optimal levels have been reached before proceeding to Phase 3 (if chief complaints still exist)

Phase 3—Eradication:
3a—Gut Therapy

Phase 3 takes substantially more time and usually require some sort of eradication of unwanted pathogens as opposed to the other two Phases (which take effect almost instantaneously and require little to no "die-off"). It is only necessary if ailments persist through Phase 1 and Phase 2. The gut should be addressed before pathogens because it causes less harm on the body as a whole.

The "die-off" effect, known as a Herxheimer. Reaction (HX), ensues as a result of attacking toxins and pathogens in order to eradicate them from the system. Specifically, it is known as the reaction to toxins being released after a toxic organism is killed. Once attacked, they give off one last effort as they die, releasing all of their toxins. The toxins have nowhere to go but to be released into your body, thus causing an unwanted rise in glutamate and other excitatory chemicals, subsequently causing a dramatic increase in electricity.

Additionally, if these chemicals remain at high levels, it will cause the hormones to re-suppress as well as plummeting the restored calming chemicals (neurotransmitters) (see FIG. 3). This effect is extremely dangerous and is exemplified when treating the gut or pathogens. Although necessary at times to eradicate unwanted pathogens and bacteria, this reaction must be minimized as much as possible in order to protect the brain. The process is roughly as follows:

The key to a smooth and effective treatment that protects the brain and body is to monitor yourself throughout the process and ease yourself through this cleanse. FIX reactions can be extremely dangerous—you must stop and re-heal if this reaction persists for 3-4 days or if the reaction grows worse. This process does require ample attention to detail; however, it is designed in a manner to ease individuals into this cleanse and more importantly protect the brain.

The oral supplementation regimen outlined in Phase 1c should be taken throughout this process to further protect the brain and body.

First—two weeks—Add a probiotic, approximately 15-50 billion, for two weeks. Start slow, if no HX reaction has occurred at the end of the two week period then proceed to the second step. Continue the probiotic through the entire gut protocol.

Second—two weeks—Add Caprylic Acid. Take for two days, then two capsules for the next 3 days in preparation for 3 capsules a day on the $6^{th}$ day. Take 3 capsules a day for the next six weeks (or until empty). Caprylic Acid loses its efficacy after 6 weeks—it should not be continued past this period. Once two weeks have elapsed, proceed to the third step.

Third—Duration of Supplement—Add CandiGone by RenewLife. This product helps kill all the remaining yeast as well as other unwanted bacteria and overgrowth in the gut. Start by taking the drops first—ten (10) drops for 3 days and then twenty (20) drops for the next 3 days. On the $7^{th}$ day (start of week 6 of the total cleanse), take thirty (30) drops for 3 more days. Then add one capsule in addition to the thirty (30) drops for the next 3 days. Once these 3 days have been completed, take the two capsules with the thirty drops for the duration of the product (approximately 4 weeks).

This entire process should take approximately 8-10 weeks. The gut is extremely difficult to heal and requires time to heal properly—usually 1-2 years or more. Although the entire process takes 1-2 years or more, this protocol will help "jumpstart" the process. The additional time for healing (1-2 years) will help with the remaining healing period. Most feel substantially better after the 10 week process; however some may need to repeat the third step (or repeat the process entirely) due to massive overgrowth in the gut.

3b—Pathogenic Eradication

This step must not be taken lightly as many who proceed to this step have massive overgrowth of pathogens and thus will endure a large HX reaction throughout the following protocol. It is not a last resort in the regard that it is a "longshot" to be effective; it is a last resort due to its high risk of damaging the brain. The physician must monitor the patient at least twice daily upon administration of this protocol. The following is an intravenous therapy.

The key to a smooth and effective treatment that protects the brain and body is to monitor yourself throughout the process and ease yourself through this cleanse. HX reactions can be extremely dangerous—you must stop and re-heal if this reaction persists for 1-2 days or if the reaction grows worse. This process does require ample attention to detail; however, it is designed in a manner to ease individuals into this cleanse and more importantly protect the brain.

The oral supplementation regimen should be taken on any day that the Phase 1 IV drip is not administered.

1st week
Monday and Tuesday
Vitamin C—15,000 mg
Wednesday
Phase 1 IV Drip

Each sequential week should consist of increasing the Vitamin C by 5000-10,000 mg each week with the same schedule until 100,000 mg is reached. The protocol should stop as soon as chief complaints are alleviated even is 100,000 mg has not been reached. Additional supplementation such as lumbrokinase to help dissolve the biofilm and thin the blood to allow for better blood flow during the process can be utilized.

After each of these phases has been completed, Phase 1c can be repeated for 1-3 weeks if necessary and at the discretion of the physician; however, this step is not included in the overall invention. Additionally, before treatment ends, Phase 1a (202 on FIG. 2) should be repeated. This is the end of this invention even if the chief complaints still persist through Phase 3.

The above and other objects, features and advantages of the present invention should become even more readily apparent to those skilled in the art upon a reading of the following detailed description in conjunction with the drawings wherein there is shown and described illustrative embodiments of the invention.

Having thus described my invention, I claim:

1. A method for treatment of a patient for exposure to toxins, said method comprising the steps of:
   a. performing quantitative testing on the patient to determine toxicity and pathogenic exposure wherein said quantitative testing comprises performing genetic testing on the patient to determine a specific presence of a subset of HLA-DRB-DQB gene for lipid soluble toxin susceptibility;
   b. performing quantitative testing on the patient to determine toxicity and pathogenic exposure wherein said quantitative testing comprises performing a neurotransmitter profile on the patient to determine excitatory neurotransmitters and inhibitory neurotransmitters to determine an overall electrical state of the patient's brain;
   c. performing quantitative testing on the patient to determine toxicity and pathogenic exposure wherein said quantitative testing comprises performing an amino acid profile on the patient;
   d. performing quantitative testing on the patient to determine toxicity and pathogenic exposure wherein said quantitative testing comprises performing a hormonal profile on the patient to determine levels of Pregnenolone, Progesterone, Testosterone, Dehydroepiandrosterone Sulfate, Alpha Melanocyte Stimulating Hormone, Adrenocorticotropic Hormone, Insulin-like Growth Factor 1, Prolactin, Vitamin D, Glucose-6-phosphate Dehydrogenase Deficiency and Estrone,
   e. performing quantitative testing on the patient to determine toxicity and pathogenic exposure wherein said quantitative testing comprises performing a metabolic panel on the patient;
   f. performing quantitative testing on the patient to determine toxicity and pathogenic exposure wherein said quantitative testing comprises performing a mycotoxin profile on the patient; and
   g. returning the patient's health to an equilibrium wherein symptoms caused by exposure to toxins are no longer being experienced by the patient by administering an intravenous drip to the patient comprising Hydroxocobalamin, Pyridoxine Hydrochloride, Dexpanthenol, B Complex, Thiamine Hydrochloride, Riboflavin, Niacinamide, Vitamin C, Manganese, Zinc, Chromium, Selenium, Magnesium, L-Taurine, L-Tryptophan, L-Glutathione, L-Methionine, N-Acetyl Cysteine and L-Theanine.

2. The method of claim 1 wherein:
said intravenous drip further comprises L-Arginine, L-Lysine and Lipoic Acid.

3. The method of claim 1 further comprising a step of:
providing the patient with oral hormonal therapy.

4. The method of claim 1 further comprising a step of:
providing the patient with transdermal hormonal therapy.

5. The method of claim 1 further comprising a step of:
providing the patient with gut therapy.

6. The method of claim 1 further comprising a step of:
providing the patient with pathogenic eradication.

7. The method of claim 1 further comprising a step of:
performing quantitative testing on the patient to determine toxicity and pathogenic exposure wherein said quantitative testing comprises performing a blood analysis on the patient to determine levels Estradiol.

8. The method of claim 1 further comprising a step of:
performing quantitative testing on the patient to determine toxicity and pathogenic exposure wherein said quantitative testing comprises performing a blood analysis on the patient to determine levels of Prostate-specific Antigen.

9. A system for treatment of a patient for exposure to toxins comprising:
quantitative testing being performed on the patient to determine toxicity and pathogenic exposure wherein said quantitative testing comprises performing genetic testing on the patient to determine a specific presence of a subset of HLA-DRB-DQB gene for lipid soluble toxin susceptibility;
quantitative testing being performed on the patient to determine toxicity and pathogenic exposure wherein said quantitative testing comprises performing a neurotransmitter profile on the patient to determine excitatory neurotransmitters and inhibitory neurotransmitters to determine an overall electrical state of the patient's brain;
quantitative testing being performed on the patient to determine toxicity and pathogenic exposure wherein said quantitative testing comprises performing an amino acid profile on the patient;
quantitative testing being performed on the patient to determine toxicity and pathogenic exposure wherein said quantitative testing comprises performing a hormonal profile on the patient to determine levels of Pregnenolone, Progesterone, Testosterone, Dehydroepiandrosterone Sulfate, Alpha Melanocyte Stimulating Hormone, Adrenocorticotropic Hormone, Insulin-like Growth Factor 1, Prolactin, Vitamin D, Glucose-6-phosphate Dehydrogenase Deficiency and Estrone;

quantitative testing being performed on the patient to determine toxicity and pathogenic exposure wherein said quantitative testing comprises performing a metabolic panel on the patient;

quantitative testing being performed on the patient to determine toxicity and pathogenic exposure wherein said quantitative testing comprises performing a mycotoxin profile on the patient; and the patient's health being returned to an equilibrium wherein symptoms caused by exposure to toxins are no longer being experienced by the patient by an intravenous drip to the patient comprising Hydroxocobalamin, Pyridoxine Hydrochloride, Dexpanthenol, B Complex, Thiamine Hydrochloride, Riboflavin, Niacinamide, Vitamin C, Manganese, Zinc, Chromium, Selenium, Magnesium, L-Taurine, L-Tryptophan, L-Glutathione, L-Methionine, N-Acetyl Cysteine and L-Theanine.

10. The system of claim 9 wherein:
said intravenous drip further comprises L-Arginine, L-Lysine and Lipoic Acid.

11. The system of claim 9 further comprising:
the patient being provided with oral hormonal therapy.

12. The system of claim 9 further comprising:
the patient being provided with transdermal hormonal therapy.

13. The system of claim 9 further comprising:
the patient being provided with gut therapy.

14. The system of claim 9 further comprising:
the patient being provided with pathogenic eradication.

15. The system of claim 9 further comprising:
quantitative testing being performed on the patient to determine toxicity and pathogenic exposure wherein said quantitative testing comprises performing a blood analysis on the patient to determine levels Estradiol.

16. The system of claim 9 further comprising:
quantitative testing being performed on the patient to determine toxicity and pathogenic exposure wherein said quantitative testing comprises performing a blood analysis on the patient to determine levels of Prostate-specific Antigen.

* * * * *